US006077447A

United States Patent [19]

Coelho et al.

[11] Patent Number: 6,077,447

[45] Date of Patent: Jun. 20, 2000

[54] FIBRINOGEN APPARATUS, METHOD AND CONTAINER

[75] Inventors: Philip H. Coelho, El Dorado Hills; Terry L. Wolf, Placerville; Curtis D. Mau, Rancho Cordova, all of Calif.; Jeffery D. Arnett, Ypsilanti; Richard F. Huyser, Kalamazoo, both of Mich.

[73] Assignee: ThermoGenesis Corp., Rancho Cordova, Calif.

[21] Appl. No.: 09/235,234

[22] Filed: Jan. 22, 1999

Related U.S. Application Data

[63] Continuation of application No. 08/653,356, May 24, 1996, abandoned.

[51] Int. Cl.[7] .......................... B01D 17/00; B01D 57/00; A61M 1/36

[52] U.S. Cl. .......................... 210/774; 210/85; 210/175; 210/177; 210/178; 210/180; 210/256; 210/258; 210/261; 210/416.1; 210/436; 210/472; 210/739; 210/742; 210/774; 62/56; 62/68; 422/101; 422/102; 422/105; 422/285; 435/2; 530/382; 604/403

[58] Field of Search .................................... 210/175, 177, 210/178, 180, 256, 258, 261, 416.1, 436, 472, 473, 774, 787, 739, 742, 85; 422/105, 109, 255, 258, 99, 101, 102; 62/56, 57, 66, 68, 342, 346, 532, 538; 435/2; 128/276; 530/427, 382; 604/113, 114, 403

[56] References Cited

U.S. PATENT DOCUMENTS

| | | |
|---|---|---|
| 2,845,929 | 8/1958 | Strumia . |
| 3,839,204 | 10/1974 | Ingenito et al. . |
| 4,025,618 | 5/1977 | Garber et al. . |
| 4,386,504 | 6/1983 | Brätigam . |
| 4,801,777 | 1/1989 | Auerbach . |
| 4,915,847 | 4/1990 | Dillon et al. . |
| 5,261,255 | 11/1993 | Coelho et al. . |
| 5,462,716 | 10/1995 | Holm . |
| 5,482,854 | 1/1996 | O'Leary et al. . |
| 5,520,885 | 5/1996 | Coelho et al. . |

FOREIGN PATENT DOCUMENTS

| | | |
|---|---|---|
| 578533 | 10/1977 | Russian Federation . |

*Primary Examiner*—John Kim
*Attorney, Agent, or Firm*—Bernard Kreten

[57] ABSTRACT

A device for producing fibrinogen includes a platen having a surface configured for heat exchange with a container, which is adhered to the platen by device of a vacuum and heat exchange allowing both cooling and heating to occur along the boundary between the container and the platen. The platen is operatively coupled to a device of rocking the platen about a horizontal axis and the container allows scavenging of a cryoprecipitate fibrinogen from the blood product for subsequent utilization. A method for fabricating fibrinogen is also disclosed, including the steps of receiving blood product in a container having a heat transfer surface thereon, adhering a container to a heat transfer platen, rocking the container and coating the interior of the container with blood product, transferring heat and thereby altering the temperature of the platen, sensing the temperature of the platen and monitoring the platen temperature, and coupling the heat transfer to the temperature sensor and cycling the blood product through a phase change.

72 Claims, 3 Drawing Sheets

FIBRINOGEN APPARATUS, METHOD AND CONTAINER

This application is a continuation of U.S. patent application Ser. No. 08/653,356, abandoned.

FIELD OF THE INVENTION

The following invention reflects an apparatus, system and method for fractionating from whole blood, plasma or other blood products the clotting factor known as fibrinogen. An apparatus is disclosed which receives a container for optimum heat exchange contact and orients the container in tangential relation with a platen on a substantially planar surface thereof which includes means for oscillation.

BACKGROUND OF THE INVENTION

Fibrinogen can be extremely useful in surgical environments for sealing incisions and binding wounds. A need exists to deliver fibrinogen in a timely manner during a surgical procedure which is of the highest quality.

Autologous blood donation is preferred since it removes potential sources of interferences with respect to the quality of the fibrinogen product. Like most blood products, fibrinogen is thermolabile and must be harvested and processed under optimal conditions to maintain a high quality profile.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
|---|---|---|
| 2,845,929 | August 5, 1958 | Strumia |
| 3,839,204 | October 1, 1974 | Ingenito, et al. |
| 4,025,618 | May 24, 1977 | Garber, et al. |
| 4,801,777 | January 31, 1989 | Auerbach |
| 4,915,847 | April 10, 1990 | Dillon, et al. |
| 5,261,255 | November 16, 1993 | Coelho, et al. |
| 5,462,716 | October 31, 1995 | Holm |
| 5,482,854 | January 9, 1996 | O'Leary, et al. |
| 5,520,885 | May 28, 1996 | Coelho, et al. |

SUMMARY OF THE INVENTION

The instant invention provides a high quality product in a timely manner. In many operating environments, the blood of the person undergoing an operation is frequently predeposited or scavenged, cleaned and returned to the patient during the surgical process thereby minimizing the demand on third party blood sources. The speed with which the instant invention operates allows the clotting protiens, including fibrinogen to be extracted from the predeposited or scavenged blood of the patient during the operating procedure and allows the residual to be delivered back to the patient after the fibrinogen has been extracted therefrom and sequestered for use in closing an incision at the end of the operating procedure.

One focal point of the instant invention is a platen which receives a container on a top surface thereof and processes the blood product contained within the container for the formation of fibrinogen. A top surface of the platen includes a means to tightly engage the container to its upper surface. A vacuum is formed between the top surface of the platen and an underside of the container which is formed from pliant material. The vacuum is applied through a series of grooves strategically deployed on the top surface of the platen to hold the bottom surface of the container in tight registry. As the vacuum is being pulled, the pliant bottom surface of the container adheres tightly and in good thermal conductive relationship with the platen.

The platen includes means for heating and cooling the contents of the container through the pliant bottom surface of the container. The container is also strategically dimensioned to include ullage or an air space so that the pliant bottom surface of the container will receive a thin coating of the blood product thereon when the container is rocked by the platen. The platen is supported on a means for rocking the platen about a horizontal axis in accordance with a temperature responsive protocol to take the container through various temperature profiles and therefore the blood product contained therewithin. As the platen rocks or oscillates about a horizontal axis, the container is constrained to move in a similar fashion allowing the blood product to splash on an interior of the bottom surface while enjoying good thermal heat transfer between the platen and the container.

The container includes a passageway for receiving the blood product and returning supernatant, an outlet operatively coupled to a syringe for receiving the fibrinogen resulting from the heating, cooling and rocking process and a vent on a surface of the container opposite from the bottom surface is provided with a filter element to take into account aspiration and pressure differentials between the interior of the container and the exterior.

OBJECTS OF THE INVENTION

Accordingly, it is a primary object of the present invention to provide a novel and useful apparatus for producing fibrinogen and a method therefore.

A further object of the present invention is to provide a device as characterized above which is extremely reliable in use and to a large degree automated thereby allowing the device to be used in a foolproof manner.

A further object of the present invention is to provide a device as characterized above which operates at an extremely rapid pace so that the fibrinogen fabrication can proceed in a timely manner vis-a-vis a surgical procedure whereby fibrinogen is ready for the operation procedure itself.

A further object of the present invention is to provide a device as characterized above which preserves the blood product and the fibrinogen at a very high level of quality.

Viewed from a first vantage point, it is an object of the present invention to provide an apparatus for extracting fibrinogen from a blood product, comprising, in combination: a platen, heat exchange means coupled to the platen, a container, means on the platen to retain the container on the platen in heat exchange relationship, and means for facilitating extraction of fibrinogen from the container coupled to the apparatus.

Viewed from a second vantage point, it is an object of the present invention to provide a system for fabricating fibrinogen, comprising, in combination: a container receiving blood product therein, the container having a heat transfer surface, a means to adhere the container to a heat transfer platen, means to rock the container to coat the heat transfer surface of the container, heat transfer means altering the temperature of the platen, temperature sensing means on the platen to monitor platen temperature, and control means coupling the heat transfer means to the temperature means to cycle the blood product through phase change.

Viewed from a second vantage point, it is an object of the present invention to provide a method for extracting fibrinogen, the steps including: placing a blood product into a container having a bottom surface with heat conductive capability, placing the container onto a heat transfer platen, altering the temperature of the platen using a heat transfer algorithm including measuring the temperature of the platen as a benchmark for moving to successive phases, and removing the fibrinogen from the container.

These and other objects will be made manifest when considering the following detailed specification when taken in conjunction with the appended drawing figures.

DESCRIPTION OF PREFERRED EMBODIMENTS

Figure 1:
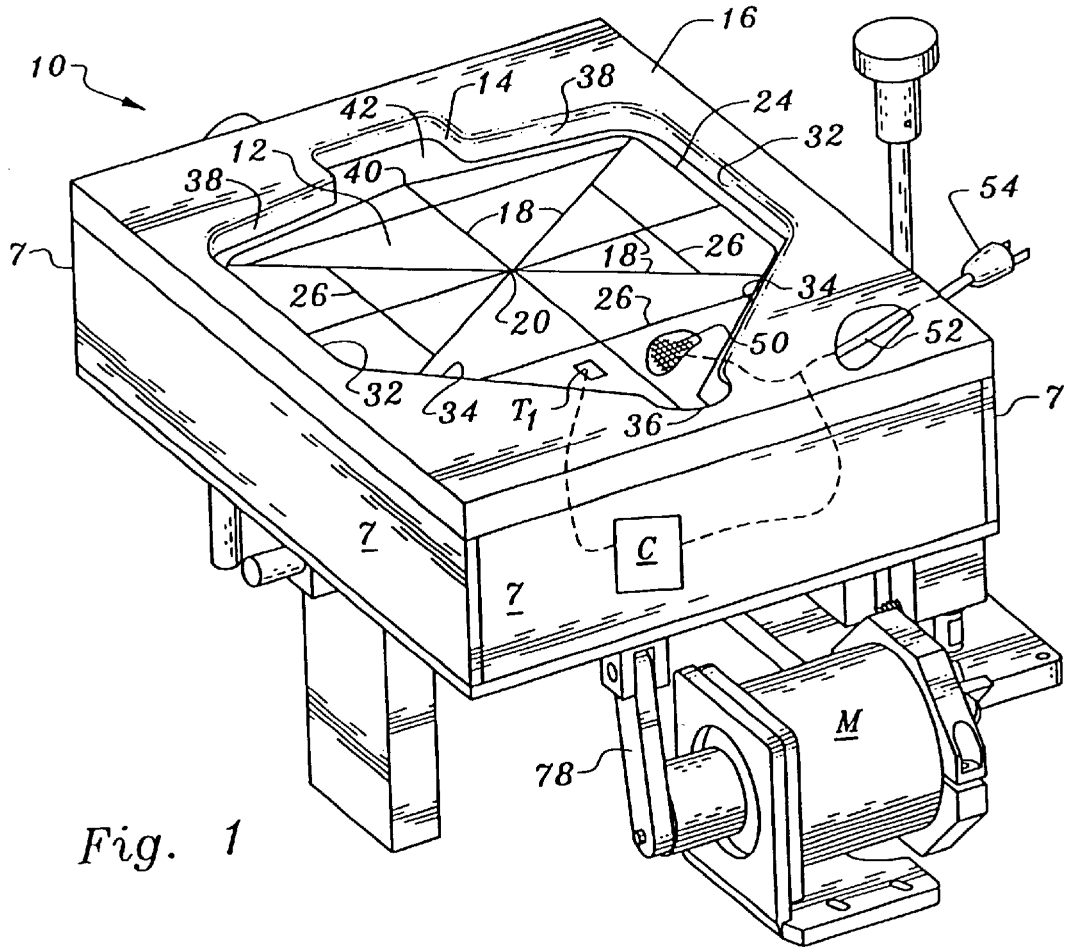
FIG. 1 is a perspective view of the apparatus according to the present invention.

Considering the drawings, wherein like reference numerals denote like parts throughout the various drawing figures, reference numeral 10 is directed to the heat transfer apparatus according to the present invention. Reference numeral 100 is directed to the container associated therewith.

In its essence, the heat transfer apparatus 10 includes a platen 12 having a substantially planar top surface which is adapted to receive a bottom surface 112 of the container 100. The platen is configured to have a peripheral wall 14 that mirrors the periphery 114 of the container 100. Thus, the container 100 nests within a recess defined by the platen 12 and peripheral wall 14 circumscribing the platen. The periphery 14 terminates in a top surface 16 which is substantially parallel to and horizontally spaced from the top surface 116 of the platen 12.

The top surface of the platen 12 includes a means for forming a vacuum on the top surface thereof to assure excellent tangential registry with a pliant bottom surface 112 of the container 100. The means for applying the vacuum includes a plurality of grooves 18 radiating from a central vacuum point 20 where the vacuum appears. Viewing FIG. 3, a vacuum access outlet to a vacuum pump (VP) is shown so that negative pressure exists along the passageways of grooves 18 caused by the vacuum. This sucks the pliant bottom surface 112 of the container in tight registry with the platen for good thermal conduct. In addition to the grooves 18 radiating from the central vacuum point 20, a peripheral groove 24 underlies a corresponding periphery of the container 100, just inboard from a peripheral flange 114 of the container. The peripheral flange 114 of the container has the rigidity associated with its top wall 116 and therefore the peripheral groove 24 is just inboard of the peripheral flange and is thus still capable of effecting the pliant bottom surface 112 of the container 100. In a preferred form of the invention, eight radial grooves 18 emanate from the central vacuum point 20 spaced 45° apart and extend to the peripheral groove 24. In addition, transverse secant-type grooves 26 bridge between radial grooves 18 to enhance the vacuum. As shown, the recess associated with the platen has a substantially pentagonal or hexagonal shape where two substantially spaced parallel side walls 32 truncate to a apex 36 by means of converging walls 34 which converge to the apex 36. Opposite the apex 36 is a top wall formed from two walls 38 which are not precisely collinear, but converge upwardly to a point 40. A shelf 42 on the platen above the point 40 accommodates a support tab 142 on a container which allows the container to be supported or hung up by means of a plurality of holes 144. This end of the container also includes tubing 146 and a spike 148 to receive the blood product therewithin, admitting the blood product to an interior of the container 100. Subsequently, as to be explained, supernatant is drawn from tubing 146 for retransfusion to the patient.

In addition to the vacuum on the platen 12, the platen is formed from a heat conductive material, such as a conductive metal and may have embedded therein a series of heating elements such as resistive heat elements to allow heat to be transferred from the platen to the interior of the container 100 via the pliant bottom surface 112. More particularly, as shown in FIG. 1, a fragmented view reveals a portion of a heating element 50 which permeates the entire top surface of the platen. A source of power (not shown) is operatively coupled to the heating element by means of a conductor 52, where the conductor includes an outlet plug 54 for changing the temperature profile of the platen.

Figure 2:
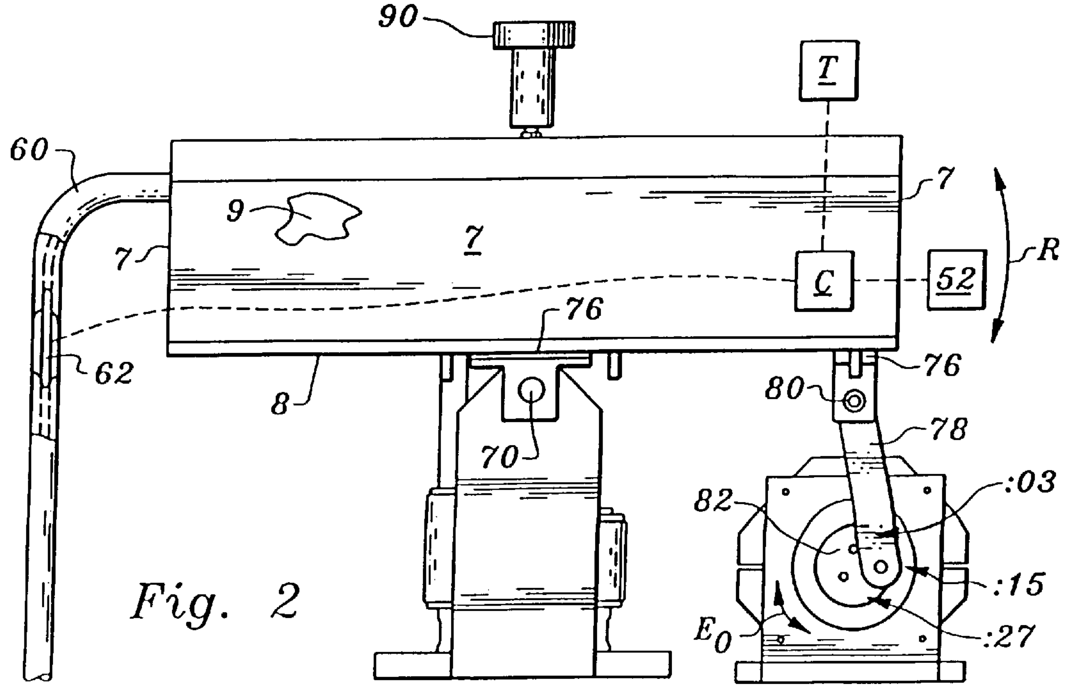
FIG. 2 is a side view thereof.

With respect to FIG. 2, this side view shows the means for inputting cooling preferably via a pair of concentric conduits 60 and 62. A liquid, such as freon, enters into the apparatus 10 on a bottom side of the platen 12 via conduit 62. A hollow 9 exists below the platen 12, above a bottom wall 8 and surrounded by side walls 7. Once it vaporizes, providing heat transfer, the freon is scavenged via the outer, concentric tube 60 for subsequent reliquification. This conduit system could also introduce hot fluid for heating in lieu of heater 50.

Referring back to FIG. 1, a temperature sensor T is operatively coupled to a top surface of the platen 12. This temperature sensor T is also operatively coupled to both the heating element 50 and to the refrigeration system 60, 62. A controller C is interposed between the temperature monitor and both the heater 50 and the cooler 60. The controller includes a logic circuit for optimizing fibrinogen production as suggested by the graph of FIG. 4 and to be described hereinafter. The controller C also is operatively coupled to a motor M which regulates the manner in which the motor M will cause the platen 12 to move in a manner now to be described.

Figure 3:
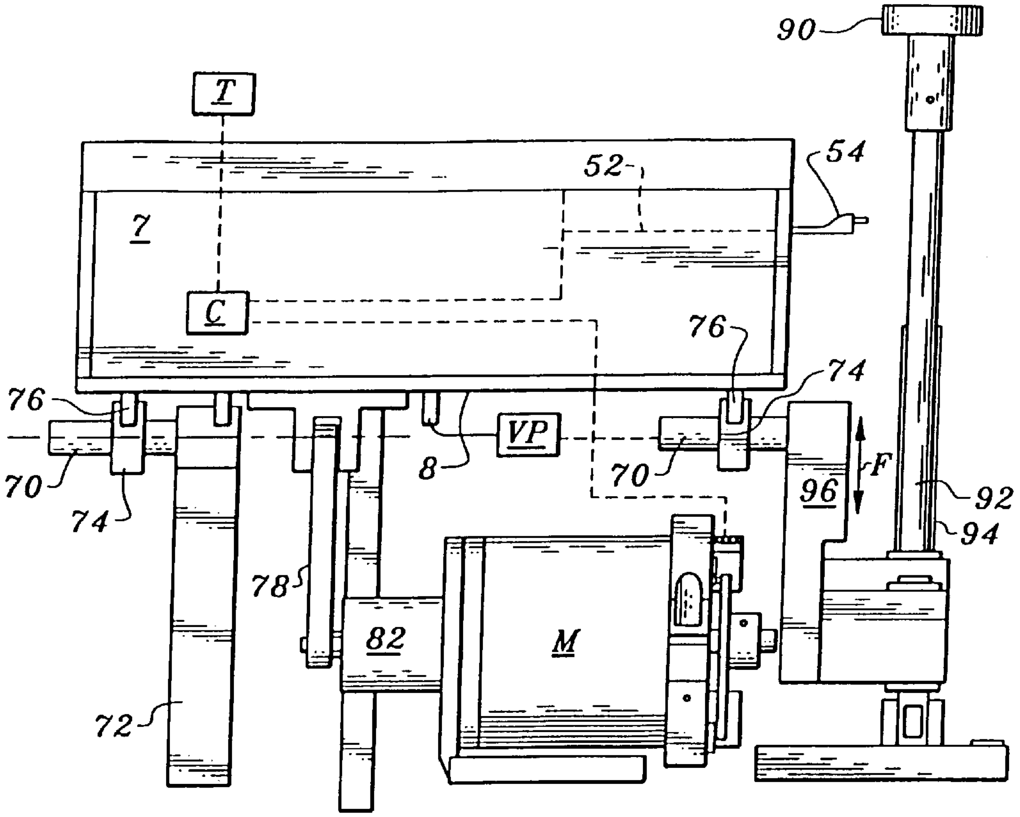
FIG. 3 is an end view thereof.

As mentioned, means to cause the platen to move are provided, and more specifically, a means to rock the platen about a horizontal axis is preferred. Viewing first FIG. 3, a horizontal axis 70 is shown which allows the platen to rock in the direction of the double ended arrow R shown in FIG. 2. It is preferred that the horizontal axle 70 be formed from two parts, each supported on a separate stand. One stand 72 is shown in FIG. 3 on the left-hand side thereof which supports the shaft 70 which in turn supports a bearing 74 attached to a bottom surface 8 of an open top box within which the platen is exposed as its open top surface. The box bottom 8 includes a downwardly extending tab 76 forming a saddle overlying the bearing 74. Similarly, the right-hand side of FIG. 3 shows a similar bearing 74 and saddle 76 underlying the box and attached to the bottom surface to support the box yet still allow rotation of the box about the direction of the double ended arrow R. A third area of support includes the rocker structure 76 attached to an edge or nose of the box at its bottom surface 8 nearest the apex 36 mentioned with respect to FIG. 1. The rocker portion includes a crank arm 78 connected to a downwardly extending tab 80 emanating from a bottom surface 8 of the box, the crank 78 operatively coupled to an output shaft of motor M via an eccentric cam 82. Thus, the crank arm will follow the direction of rotation of the cam about the double ended arrow E. For subsequent discussion, please note that in FIG. 2 the crank arm 78 is connected to the eccentric 82 at approximately a "15 minute after the hour position".

Because it is desired that the horizontal axis 70 be substantially horizontal and not skewed to one side or the other, a means for adjusting the elevation of one side is shown in FIG. 3. A hand wheel 90 rotates a threaded shaft 92 which is operatively coupled to a threaded sleeve 94. The threaded shaft 92 allows vertical translation of the sleeve in the direction of the double ended arrow F. This transfers to link 96 which is coupled to the threaded sleeve 94. Thus, rotation of the shaft 92 via hand wheel 90 will cause the sleeve 94 to translate vertically along the direction of the double ended arrow F, and by its rigid interconnection with the link 96 that carries the horizontal shaft 70 on the right-hand side thereof will allow similar motion of that shaft 70 assuring that the right-hand side of the box is level with the left-hand side of the box. This precludes the unwanted pooling of blood product on one side or the other of the container rather than ultimately at the apex 36 of the platen or the shelf 42.

Figure 5:
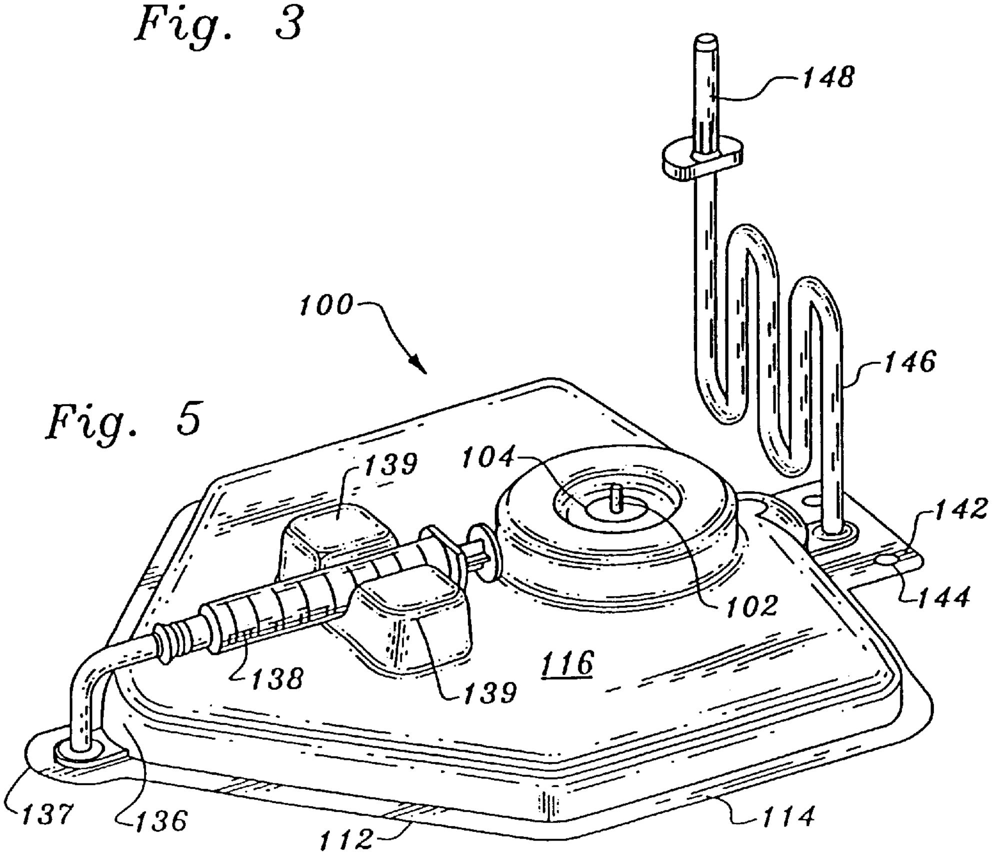
FIG. 5 is a perspective view of one container suitable for use in the apparatus according to the present invention.

With respect to FIG. 5, more detail on the container 100 is shown. More specifically, an apex 136 of the container is adapted to overlie the apex 36 in the platen. A lower marginal portion 137 allows fluid communication and support for a syringe 138 so that some contents within the container 100 can be selectively admitted into the syringe 138. The syringe 138 is held in place during storage via a pair of upwardly extending projections 139 which straddle each side of a barrel portion of the syringe, holding it in place. In addition, the container 100 includes a vent 102 having a filter element 104 therewithin to allow aspiration within the interior of the container 100 as would be necessitated due to the changes within the interior pressure based for example, on the cyclic heating and cooling.

Figure 4:
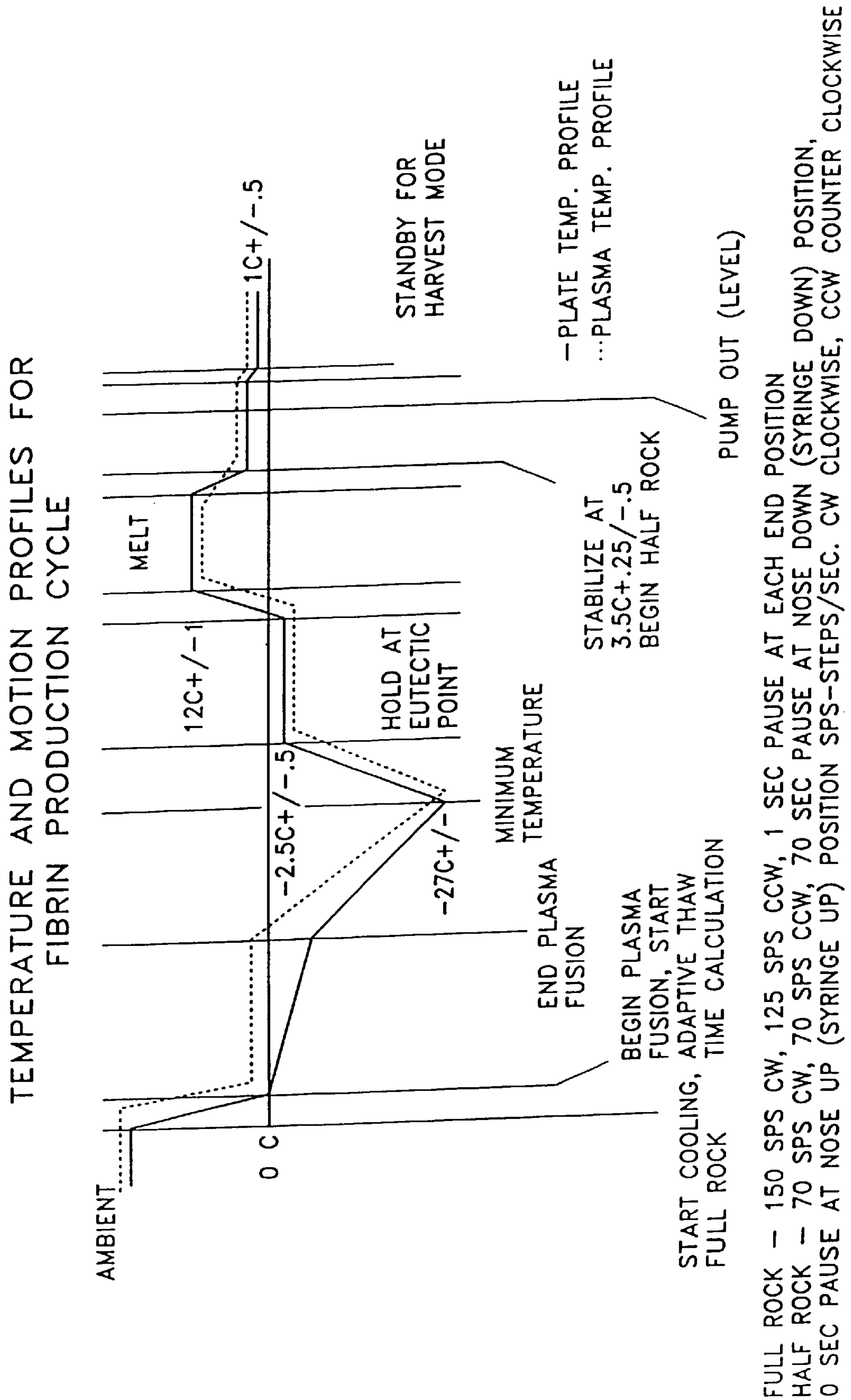
FIG. 4 is a diagrammatic profile of one heat transfer algorithm for production of the fibrinogen.

FIG. 4 shows an optimized algorithm graphically for controlling the heating and cooling regimen for the production of optimum, high quality fibrinogen. As shown in FIG. 4, the blood product is originally taken in at "ambient" conditions and its temperature is decreased by use of the cooling fluid (e.g. freon) via conduit 62 within the interior of the box of the apparatus 10. It is to be noted that when the slope of the cooling curve for the platen first changes at the cross over point of 0° C. This corresponds with the inception of plasma fusion and is reflected by a change in the slope of the temperature decrease of the platen. While it is possible to monitor the temperature profile of the fibrinogen, it has been found that monitoring the platen is preferred for several reasons. First, it prevents potential contamination of the fibrinogen and blood product with a temperature sensor and second it has been found that the temperature change of the platen is a very reliable indicator of the change of phase in temperature profile of the plasma as shown in FIG. 4. Once the plasma has reached the end of the plasma fusion stage, the slope of the curve for the plasma temperature profile again changes and is allowed to decrease to −27° C. (plus or minus 1 degree). This is the minimum temperature for the preferred process. At this point, the temperature is increased either by using the electrical heating 50 shown in FIG. 1 and/or by diverting hot fluid into conduit 62. This temperature rise is allowed to increase until −2.5° C. (plus or minus 0.5 degrees). Next the temperature is held constant at the eutectic point. Next, the plasma is allowed to rise in temperature so that the platen registers a temperature of 12° C. (plus or minus 1 degree) and it is held at this temperature while the plasma is allowed to melt. Next, the plate temperature profile is allowed to drop back to 3.5° C. (plus 2.5 degrees, minus 0.5 degrees) and at this point, a change in the rocking protocol about the horizontal axis will occur. Up to this point, the platen 12 has been allowed to enjoy a "full rock" which is to say rotation of the cam in FIG. 2 from one extreme position (0.03) to a second extreme position (0.27) and back along the direction of the double ended arrows E. Stated alternatively, if the cam 82 were the face of a clock, the extreme position for full rock occurs between "three minutes after the hour" and "twenty-seven minutes after the hour." Full rock allows the bed and platen to move along the double ended arrow R above and below the horizontal plane so that there is declination of the platen on both sides of the axis of rotation exemplified by axle 70. At the last named point on FIG. 4, where the 3.5° C. stabilization has taken place, a "half rock" cycle now begins in which the rocking is allowed to occur only between 0.03 and 0.15. That is, regarding FIG. 2, the cam is allowed to rock only from "three minutes after the hour" and "fifteen minutes after the hour" allowing only declination and to the right-hand side of the bed. The platen of FIG. 2 thereby migrates the fibrinogen to the apex area of both the platen apex 36 and the container bag 136. This allows the fibrinogen to be collected at the bottom of the container 100 and extracted into the syringe 138 for subsequent use. While the "half rock" cycle begins, the temperature is held constant at 3.5° C. Note the "pump out" phase in FIG. 4, with the platen held in a horizontal plane, supernatant is expressed out of container 100 via tubing 146. Thereafter, the apex 36 is above the horizontal plane to further drain the last of the supernatant. Lastly a final dip in the temperature to 1° C. (plus or minus 0.5 degrees) occurs to allow harvest.

In use and operation, the container 100 is filled with the blood plasma using the spike 148. The container 100 is placed within the peripheral wall 14 and on top of the platen 12 and a vacuum is drawn via vacuum port 20. Thereafter, the cycle described in FIG. 4 is effected utilizing the controller C coupled to the temperature probe T, heating element 50 (or hot fluid admission within conduit 62) and coupled with the cold fluid admission into conduit 62 followed by scavenging via exhaust conduit 60. The controller C also operatively coupled to the motor M causes the rocking protocol set forth hereinabove.

Having thus described the invention, it should be apparent that numerous structural modifications and adaptations may be resorted to without departing from the scope and fair meaning of the instant invention as set forth hereinabove and as described hereinbelow by the claims.

I claim:

1. An apparatus for extracting fibrinogen from a blood product, comprising, in combination:

a platen having a surface, heat exchange means coupled to said platen, a container having a pliant surface substantially coextensive with said platen surface, said container initially loaded with fibrinogen containing blood product, means on said platen to retain said container on said platen in heat exchange relationship, said heat exchange means causing the fibrinogen to be distinct from the residual blood product, and means for extracting fibrinogen from said container and residual blood product coupled to said apparatus.

2. The apparatus of claim 1 wherein said platen retaining means includes a vacuum port passing through a top surface of said platen and communicating with a plurality of grooves formed on said top surface of said platen, said container having a bottom surface adapted to lie on said platen and be adhered thereto by a vacuum being formed.

3. The apparatus of claim 2 wherein said platen includes a temperature sensor located adjacent a top surface and in operative heat conductive relationship therewith to monitor the temperature of said platen.

4. The apparatus of claim 3 wherein said platen is in operative communication with a heating means for heating said platen.

5. The apparatus of claim 4 wherein said platen is in operative communication with a cooling means for cooling said platen.

6. The apparatus of claim 5 wherein said platen is operatively coupled to a means for rocking said platen about a horizontal axis.

7. The apparatus of claim 6 wherein said platen is operatively coupled to a controller which controls said heat, cooling and rocking in response to said temperature.

8. A system for fabricating fibrinogen, comprising, in combination:

a container for receiving blood product therein, said container having a pliant heat transfer surface, means to adhere the container to a heat transfer platen having a surface substantially coextensive with the container surface, means to rock said container to coat said heat transfer surface of said container with the blood product, heat transfer means altering the temperature of said platen, temperature sensing means on said platen to monitor the platen temperature, and control means coupling said heat transfer means to said temperature sensing means to cycle the blood product through phase change.

9. The system of claim 8 wherein said rocking means includes a first and second pivot point, said first and second pivot points about a common axis of rotation and amidships of said platen, and an oscillatory crank at one extremity of said platen which moves said platen about an axis of rotation, said oscillatory crank connected to a cam and driven by a motor.

10. The system of claim 9 wherein said adhering means includes a vacuum port on said platen accessing a bottom surface of said container and a vacuum means coupled to said vacuum port to draw said container down towards said platen.

11. A system for fabricating fibrinogen, comprising, in combination:

a container for receiving blood product therein, said container having a heat transfer surface, means to adhere the container to a heat transfer platen, means to rock said container to coat said heat transfer surface of said container with the blood product, heat transfer means altering the temperature of said platen, temperature sensing means on said platen to monitor the platen temperature, and control means coupling said heat transfer means to said temperature sensing means to cycle the blood product through phase change, wherein said rocking means includes a first and second pivot point, said first and second pivot points about a common axis of rotation and amidships of said platen, and an oscillatory crank at one extremity of said platen which moves said platen about an axis of rotation, said oscillatory crank connected to a cam and driven by a motor, wherein said adhering means includes a vacuum port on said platen accessing a bottom surface of said container and a vacuum means coupled to said vacuum port to draw said container down towards said platen, and wherein said vacuum port includes a plurality of grooves emanating from a central vacuum port area to enhance the area of tangency between said container and said platen.

12. The system of claim 11 wherein said grooves include a peripheral groove uniting said grooves emanating from said central vacuum port area for further adherence.

13. The system of claim 12 including secant grooves extending between said radial grooves to enhance the adherence.

14. The system of claim 13 including said heat transfer means configured as a fluid having access to a side of said platen remote from said container for contacting the fluid therewith for heat transfer to said platen.

15. The system of claim 14 including an electrical element embedded in said platen for further heat transfer.

16. The system of claim 15 wherein said plurality of grooves are radiating.

17. A method for extracting fibrinogen, the steps including:

placing a blood product into a container having a bottom pliant surface with heat conductive capability, placing the container onto a heat transfer platen having a surface substantially coextensive with the container bottom surface, altering the temperature of the platen using a heat transfer algorithm including measuring the temperature of the platen as a benchmark for moving to successive phases, and removing the fibrinogen from the container.

18. The method of claim 17 further including adhering the container to the heat transfer platen.

19. The method of claim 18 further including altering the temperature of the platen such that the platen receives blood product at substantially ambient conditions and is driven down to 0° C. upon which plasma fusion begins, dropping the temperature of the platen to −27° C. allowing the temperature to rise to −2.5° C., allowing the temperature to be held at its eutectic point and subsequently allowing the temperature to rise to a melting point of 12° C. and cooling the platen to 3.5° C. while rocking the platen about its horizontal axis such that an apex of the platen moves both above and below horizontal.

20. The method of claim 19 further including holding the temperature constant at 3.5° C. and maintaining the platen so that it rocks only such that its apex goes below the horizontal plane and returning to a level condition and holding said platen in a level condition.

21. The method of claim 20 including pumping out supernatant liquid from the container while holding the container in a substantially horizontal position.

22. The method of claim 20 including continuing rocking of the platen and container such that the apex of the container remains below a horizontal plane.

23. The method of claim 22 including holding the apex of the platen in a lower, below horizontal position and reducing the temperature to 1° C. allowing harvest of the fibrinogen via a syringe connected to the apex of the container.

24. The method of claim 23 including forming the container for sequestering fibrinogen from a blood product by:

conforming a pliant bottom surface to the platen upon which said bottom surface is located, transferring heat from said bottom surface and adhering the pliant bottom surface to the platen by vacuum, shaping said container to include an apex at one extremity, allowing fluid migration to said apex for accessing fluid which migrates to said apex for extraction.

25. The method of claim 24 including accessing fluid in the container by syringing from the apex.

26. The method of claim 25 including storing said syringe on a top surface of said container by removably attaching the syringe thereto.

27. The method of claim 26 including venting said top surface of the container.

28. The method of claim 27 including expressing supernatant from said container via a tube.

29. The method of claim 28 including hanging said container in a vertical elevation with said apex at its lowestmost position.

30. The method of claim 29 including filtering through said vent means.

31. A container for sequestering fibrinogen from a blood product comprising, in combination:

a pliant bottom surface adapted to conform to a surface of a platen upon which said bottom surface is located, said bottom surface possessing the ability for heat transfer means and flexibility to allow vacuum retention, said container shaped to include an apex at one extremity allowing fluid migration thereto and means for accessing fluid which migrates to said apex for extraction, wherein means for providing access includes a syringe in fluid communication therewith, and wherein said syringe is stored on a top surface of said container by removable attachment means.

32. The container of claim 31 including vent means on said top surface.

33. The container of claim 32 including means for expressing supernatant from said container.

34. The container of claim 33 including a support for hanging said container in a vertical elevation with said apex at its lowestmost position.

35. The container of claim 34 including a filter associated with said vent means.

36. A method for extracting fibrinogen from a blood product, comprising, in combination:

placing the blood product into a container, placing said container having a pliant surface on a platen having a surface substantially coextensive with said container surface, exchanging heat between said platen and said container to separate the fibrinogen from the blood product, fixedly adhering said container on said platen in heat exchange relationship, and extracting fibrinogen from said container.

37. The method of claim 36 wherein said adhering step includes applying a vacuum through a top surface of said platen and communicating the vacuum with a plurality of grooves formed on said top surface of said platen, forming said container with a bottom surface lying on said platen and adhering thereto by the vacuum.

38. The method of claim 37 including sensing temperature between the container and platen in operative heat conductive relationship and monitoring the temperature of said platen.

39. The method of claim 38 including heating said platen.

40. The method of claim 39 including cooling said platen.

41. The method of claim 40 including rocking said platen about a horizontal axis.

42. The method of claim 41 including controlling said heating, cooling and rocking in response to sensing said temperature.

43. A method for fabricating fibrinogen, the steps including:

receiving blood product in a container having a pliant surface, also having a heat transfer surface on said container, adhering the container to a heat transfer platen having a surface substantially coextensive with said pliant container surface, rocking the container and coating an interior heat transfer surface of the container with the blood product, transferring heat altering the temperature of said platen, sensing temperature on the platen and monitoring platen temperature, and coupling said heating transfer to said temperature sensing and cycling the blood product through phase change.

44. The method of claim 43 wherein said rocking means includes a first and second pivot point, said first and second pivot point about a common axis of rotation and amidships of said platen, and an oscillatory crank at one extremity of said platen which moves said platen about an axis of rotation, said oscillatory crank connected to a cam and driven by a motor.

45. The method of claim 44 wherein said adhering includes applying a vacuum from said platen accessing a bottom surface of said container and drawing said container down towards said platen.

46. A method for fabricating fibrinogen, the steps including:

receiving blood product in a container, having a heat transfer surface on said container, adhering the container to a heat transfer platen, rocking the container and coating an interior heat transfer surface of the container with the blood product, transferring heat altering the temperature of said platen, sensing temperature on the platen and monitoring platen temperature, and coupling said heating transfer to said temperature sensing and cycling the blood product through phase change, wherein said rocking means includes a first and second pivot point, said first and second pivot point about a common axis of rotation and amidships of said platen, and an oscillatory crank at one extremity of said platen which moves said platen about an axis of rotation, said oscillatory crank connected to a cam and driven by a motor, wherein said adhering includes applying a vacuum from said platen accessing a bottom surface of said container and drawing said container down towards said platen, and wherein said vacuuming includes emanating a plurality of radiating grooves from a central vacuum port area enhancing the area of tangency between the container and said platen.

47. The method of claim 46 includes uniting a peripheral groove with said radiating grooves for further adhering.

48. The method of claim 47 including extending secant grooves between radiating grooves enhancing the vacuum.

49. The method of claim 48 including configuring said heat transferring by fluid accessing to a side of said platen remote from said container for contacting the fluid therewith for heat transferring to the platen.

50. The method of claim 49 including an electrically heating in the platen for further heat transfer.

51. A system for fabricating fibrinogen, comprising, in combination:

a container receiving blood product therein, said container having a heat transfer surface, a means to adhere the container to a heat transfer platen, means to rock the container to coat the heat transfer surface of the container with the blood product, heat transfer means altering the temperature of said platen, temperature sensing means on the platen to monitor platen temperature, and control means coupling said heat transfer means to said temperature means to cycle the blood product through phase change, wherein said adhering means includes a vacuum port on said platen accessing a bottom surface of said container to draw said container down towards said platen, and wherein said vacuum includes a plurality of radiating channels emanating from a central vacuum port area to enhance the area of tangency between the container and said platen.

52. The system of claim 51 wherein said rocking means includes a first and second pivot point, said first and second pivot point about a common axis of rotation and amidships of said platen, and an oscillatory crank at one extremity of said platen which moves said platen about an axis of rotation, said oscillatory crank connected to a cam and driven by a motor.

53. The system of claim 51 wherein said channels include a peripheral groove uniting said radial channels for further adherence.

54. The system of claim 51 including secant grooves extending between said radial channels to enhance the vacuum.

55. The system of claim 51 including said heat transfer means configured as a fluid having access to a side of said platen remote from said container for contacting the fluid therewith for heat transfer to the platen.

56. The system of claim 51 including an electrical element embedded in said platen for further heat transfer.

57. A method for fabricating fibrinogen, the steps including:

receiving blood product in a container, having a heat transfer surface on said container, adhering the container to a heat transfer platen, rocking the container and coating an interior heat transfer surface of the container with the blood product, transferring heat altering the temperature of said platen, sensing temperature on the platen and monitoring platen temperature, and coupling said heating transfer to said temperature sensing and cycling the blood product through phase change, wherein said adhering includes applying a vacuum from said platen accessing a bottom surface of said container and drawing said container down towards said platen, and wherein said vacuuming includes emanating a plurality of grooves from a central vacuum port area enhancing the area of tangency between the container and said platen.

58. The method of claim 57 wherein said rocking step includes providing a first and second pivot point, locating said first and second pivot point about a common axis of rotation and amidships of said platen, and moving said platen about the axis of rotation using an oscillatory crank at one extremity of said platen, said oscillatory crank connecting to a cam and driving the crank by a motor.

59. The method of claim 57 wherein said grooves are radiating.

60. The method of claim 59 including uniting a peripheral groove with said radiating grooves for further adhering.

61. The method of claim 60 including extending secant grooves between radiating grooves, enhancing the vacuum.

62. The method of claim 57 including configuring said heat transferring by fluid accessing to a side of said platen remote from said container for contacting the fluid therewith for heat transferring to the platen.

63. The method of claim 57 including electrically heating the platen for further heat transfer.

64. A system for fabricating fibrinogen, comprising, in combination:

a container for receiving blood product therein, said container having a pliant heat transfer surface;

means to promote contact between said pliant heat transfer surface and a heat transfer platen having a surface substantially coextensive with said container surface;

means to rock said container to coat said heat transfer surface of said container with the blood product;

heat transfer means altering the temperature of said platen;

temperature sensing means on said platen to monitor the platen temperature; and control means coupling said heat transfer means to said temperature sensing means to cycle the blood product through a phase change.

65. The system of 64 wherein said rocking means includes a first and second pivot point, said first and second pivot points about a common axis of rotation and amidships of said platen, and an oscillatory crank at one extremity of said platen which moves said platen about an axis of rotation, said oscillatory crank connected to a cam and driven by a motor.

66. The system of claim 65 wherein said contact promotion means includes a vacuum port on said platen accessing a bottom surface of said container and a vacuum means coupled to said vacuum port to draw said container down toward said platen.

67. The system of claim 66 wherein said vacuum port includes a plurality of grooves emanating from a central vacuum port area to the area of tangency between said container and said platen.

68. The system of claim 67 wherein said plurality of grooves are radiating.

69. The system of claim 68 wherein said grooves include a peripheral groove uniting said radial grooves for further contact.

70. The system of claim 69 including secant grooves extending between said radial grooves to enhance the contact.

71. The system of claim 70 including said heat transfer means configured as a fluid having access to a side of said platen remote from said container for contacting the fluid therewith for heat transfer to said platen.

72. The system of claim 71 including an electrical element embedded in said platen for further heat transfer.

* * * * *